(12) United States Patent
Shih

(10) Patent No.: US 6,613,505 B2
(45) Date of Patent: Sep. 2, 2003

(54) COMPOSITION AND METHOD FOR DESTRUCTION OF INFETIOUS PRION PROTEINS

(75) Inventor: Jason C. H. Shih, Cary, NC (US)

(73) Assignee: BioResource International, Inc., Raleigh, NC (US)

( * ) Notice: Subject to any disclaimer, the term of this patent is extended or adjusted under 35 U.S.C. 154(b) by 16 days.

(21) Appl. No.: 09/834,284

(22) Filed: Apr. 12, 2001

(65) Prior Publication Data

US 2002/0172989 A1 Nov. 21, 2002

(51) Int. Cl.[7] ................................................. C12Q 1/00
(52) U.S. Cl. ........................ 435/4; 424/438; 424/442; 435/31; 435/183
(58) Field of Search ........................ 424/78.08, 78.17, 424/438, 442; 935/4, 31, 183

(56) References Cited

U.S. PATENT DOCUMENTS

| | | |
|---|---|---|
| 5,276,059 A | 1/1994 | Caughey et al. |
| 5,633,349 A | 5/1997 | Reichl |
| 5,756,678 A | 5/1998 | Shenoy et al. |
| 5,773,572 A | 6/1998 | Fishleigh et al. |
| 5,780,288 A | 7/1998 | Rohwer |
| 5,808,011 A | 9/1998 | Gawryl et al. |
| 5,869,469 A | 2/1999 | Szarek et al. |
| 5,914,255 A | 6/1999 | Grae |
| 5,948,763 A | 9/1999 | Soto-Jara et al. |
| 5,962,288 A | 10/1999 | Aksenov et al. |
| 5,972,328 A | 10/1999 | Kisilevsky et al. |
| 6,054,114 A | 4/2000 | Lansbury, Jr. et al. |
| 6,060,293 A | 5/2000 | Bohr et al. |
| 6,066,320 A | 5/2000 | Brentani et al. |
| 6,096,216 A | 8/2000 | Shanbrom et al. |
| 6,133,198 A | 10/2000 | Bengsch et al. |
| 6,183,740 B1 | 2/2001 | Short et al. |
| 6,191,154 B1 | 2/2001 | Landreth et al. |
| 6,191,168 B1 | 2/2001 | Rubenstein |
| 6,197,207 B1 | 3/2001 | Chapman et al. |
| 6,211,149 B1 | 4/2001 | Chesebro et al. |

FOREIGN PATENT DOCUMENTS

| | | |
|---|---|---|
| EP | 0530173 A3 | 3/1993 |
| EP | 0667352 A1 | 8/1995 |
| EP | 0764442 A1 | 3/1997 |
| JP | 11032795 A2 | 2/1999 |
| JP | 11049611 | 2/1999 |
| WO | WO9906066 A2 | 2/1999 |
| WO | WO038742 A1 | 7/2000 |
| WO | WO043782 | 7/2000 |
| WO | WO026238 A3 | 8/2000 |
| WO | WO047240 A1 | 8/2000 |
| WO | WO058344 A1 | 10/2000 |
| WO | WO109287 A2 | 2/2001 |

OTHER PUBLICATIONS

Bolton et al. Molecular charateristics of the major scrapie prion protein. Biochemistry (1984) vol. 23, pp. 5898–5906.*
Safar et al. Thermal stability and conformational transitions of scrapie amyloid (prion) protein correlate with infectivity. Protein Science (1993) vol. 2, pp. 2206–2216.*
Cheng et al. Production and characterization of keratinase of a feather–degrading B. licheniformis PWD–1. Bioscience Biotechnology Biochemistry (1995) vol. 59, No. 12, pp. 223–2243.*

(List continued on next page.)

Primary Examiner—James Housel
Assistant Examiner—Ulrike Winkler
(74) Attorney, Agent, or Firm—Yongzhi Yang; Steven J. Hultquist; Marianne Fuierer

(57) ABSTRACT

A method and composition for destruction of infectious prion proteins in tissue, by thermal/enzymatic treatment of the tissue with a prion-destructive protease. The method and composition are applicable to treatment of tissue containing or contaminated with prion protein strains associated with transmissible spongiform encephalopathy (TSE) and/or other prion protein-mediated diseases.

9 Claims, 1 Drawing Sheet

OTHER PUBLICATIONS

Proteinase K, Worthington Enzyme Manual, Ed. Von Worthington (1993) pp–340–341.*

Michael P. McKinley et al., *A Protease–Resistant Protein is a Structural Component of the Scrapie Prion*, Cell, vol. 35, pp. 57–62 (Nov. 1983).

G.D. Hunter, G.C. Millson, *Attempts to Release the Scrapie Agent from Tissue Debris*, Journal of Comparative Pathology, vol. 77, pp. 301–307 (1967).

D.M. Taylor et al., *Inactivation of the Bovine Spongiform Encephalopathy Agent by Rendering Procedures*, The Veterinary Record, vol. 137, pp. 605–610 (1995).

R.G. Rohwer, *Virus–Like Sensitivity of the Scrapie Agent to Heat Inactivation*, Science, vol. 223, pp. 600–602 (1984).

J.C. Darbord, *Inactivation of Prions in Daily Medical Practice*, Biomed Pharmacother, vol. 53, pp. 34–38 (1999).

William A. Rutala, David J. Weber, *Creutzfeldt–Jakob Disease: Recommendations for Disinfection and Sterilization*, Healthcare Epidemiology, CID 2001 : 32 (May 1), pp. 1348–1356 (2001).

C. Bellinger–Kawahara, et al., *Purified Scrapie Prions Resist Inactivation Procedures That Hydrolyze, Modify, or Shear Nucleic Acids*, Virology, vol. 160, pp. 271–274 (1987).

G.D. Sorenson, H.B. Binington, *Resistance of Murine Amyloid Fibrils to Proteolytic Enzymes*, Friday Morning, vol. 23, p. 550 (1964).

R.F. Marsh, R.P. Hanson, *Physical and Chemical Properties of the Transmissible Mink Encephalopathy Agent*, Journal of Virology, vol. 3, No. 2, pp. 176–180 (1969).

\* cited by examiner

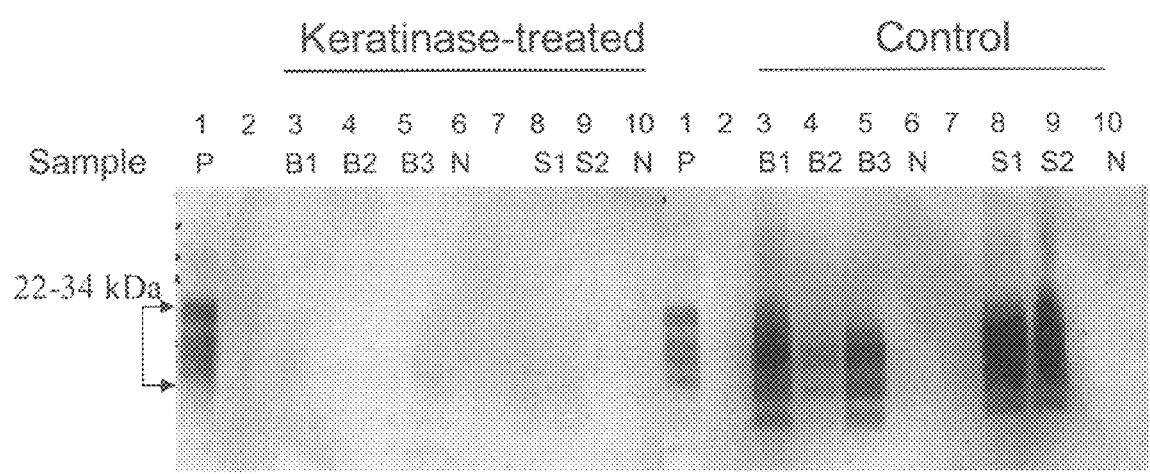

COMPOSITION AND METHOD FOR DESTRUCTION OF INFETIOUS PRION PROTEINS

FIELD OF THE INVENTION

The present invention generally relates to a composition and method for destruction of infectious prion proteins. More specifically, the invention relates to application of proteases for destruction of infectious prion proteins, such as in animal tissue containing prion proteins associated with transmissible spongiform encephalopathy (TSE), e.g., bovine spongiform encephalopathy (BSE) and sheep scrapie. The invention has application to processing of animal meat for human food and animal by-product for animal feed.

BACKGROUND OF THE INVENTION

Prion proteins are conformationally anomalous proteins that are associated with infectious neurodegenerative diseases in human as well as non-human mammalian species.

Prion diseases in non-human mammalian species include scrapie (sheep), transmissible mink encepohalopathy (minks), chronic wasting disease (elk, deer), bovine spongiform encephalopathy (BSE) (cows), feline spongiform encephalopathy (cats), and simian spongiform encephalopathy (monkeys).

In humans a variety of neurodegenerative conditions are etiologically associated with prion proteins, including Creutzfeldt-Jakob disease, Gerstmann-Straussler-Scheinker syndrome, fatal insomnia, kuru, and variant Creutzfeldt-Jakob disease. Pathogenesis of human prion diseases is associated with carnivorism (BSE-infected beef, causing new variant Creutzfeldt-Jakob disease), administration of human growth hormone (causing iatrogenic Creutzfeldt-Jakob disease) and ritualistic cannibalism (causing kuru).

Over 180,000 BSE cases and 100 human Creutzfeldt-Jakob disease cases have been reported in Europe since 1992, and the human cases are predicted to significantly rise. The spread of such disease is difficult to contain, since such disease has no cure and the pathogenic prion protein is recalcitrant and non-immunogenic. The pathogenic and infectious isoform of prion protein is very stable, rich in β-sheet structure, and resistant to heat and common proteolytic enzymes (Prusiner, S. B., Proc. Natl. Acad. Sci. U.S.A., 95, 11363 (1998); Cohen, F. E. and Prusiner, S. B., Ann. Rev. Biochem., 67, 793 (1998); and Pan, K-M, Baldwin, M., Nguyen, J., Gasset, M., Serban, A., Groth, D., Mehlhorn, I., Huang, Z., Fletterick, R. J., Cohen, F. E., and Prusiner, S. B., Proc. Natl. Acad. Sci. U.S.A, 90, 10962 (1993)).

Significant efforts have been focused on studies of BSE and prion protein contamination of human food supplies deriving from bovine sources, and of prion protein disease generation and propagation in bovine species. Infection in bovine populations has been associated with feeding of bovine herds with feedstocks containing bone meal and rendered organs and tissue deriving from infected cows, sheep and other ruminant animals.

At present, in many countries, animal products that otherwise would provide human food, and animal by-product that otherwise would provide a viable source of raw materials and nutritional supplements for animal feeds, are being incinerated and the ash residue buried, to preclude transmission of prion protein infection deriving from the presence of infectious prion proteins in associated animals.

In Europe, meat bone meal from animal by-products has been banned for feed use. In the United States, no outbreak of BSE has been reported, however, animal and rendering industries have been placed under restrictive regulations to prevent the incidence and spread of disease (Franco, B. A., Feed Stuffs, Feb. 12, 2001). Further, the United States has banned imports of meat and meat by-products.

A variety of tests for determining the presence of infectious prion proteins in animal tissue have been developed, including Western blot tests, sandwich immunoassay tests, ELISA tests, fluoroimmunoassay tests, capillary immunoelectrophoresis tests, and plasminogen binding tests (Genetic Engineering News, Vol. 21, No. 6, Mar. 15, 2001), but corresponding capability for industrially-applicable removal of infectious prion proteins from infected animal tissue has not evolved to date.

Infectious prion proteins are resistant to destruction by conventional methods that denature and otherwise degrade conformationally normal proteins, including methods such as autoclaving (even temperatures as high as 200° C. are not effective to inactivate infectious prion proteins), boiling, freezing, and exposure to reagents such as formaldehyde, carbolic acid and chloroform. Typically, incineration or treatment with bleach is employed to destroy the pathogenic isoform of the prion protein.

It therefore would be a significant advance in the art to provide a composition and methodology for destruction of infectious prion proteins, which is applicable to the treatment of biological materials, e.g., animal tissue containing or contaminated with infectious prion proteins.

SUMMARY OF THE INVENTION

The invention provides a method and composition for destruction of infectious prion proteins in tissue containing or contaminated with same.

In one aspect, the invention relates to a method of treatment of tissue associated with, i.e., containing or contaminated with, infectious prion protein ($PrP^{Sc}$). The method comprises the steps of:

(a) heating the tissue to a sufficient temperature and for sufficient time to enhance the proteolytic degradability of infective prion protein associated with the tissue; and (b) exposing the heated tissue to a proteolytic enzyme that is effective for at least partial reduction of infective prion protein associated with such tissue.

Another aspect of the invention relates to a method of enhancing degradability of an infectious prion protein by proteolytic enzymatic degradation treatment, including (a) heating the prion protein to a temperature below the pyrolytic destruction temperature of the prion protein (i.e., the temperature (>>200° C.) that is normally employed for incineration of the prion protein), followed by (b) enzymatic degradation treatment of the prion protein.

In a further aspect, the invention relates to a method of removing infective prion protein from bovine tissue containing or contaminated with same, the method including cooking the bovine tissue at a temperature in a range of from about 100° C. to about 150° C., e.g., for a time of from about 5 minutes to about 5 hours, followed by (b) exposing the bovine tissue to a proteolytic enzyme at a temperature in a range of from about 35° C. to about 100° C. at which the proteolytic enzyme is thermally stable and proteolytically effective to at least partially destroy the infective prion protein associated with the bovine tissue.

A further aspect of the invention relates to a method of degrading infectious prion protein, comprising (a) heating the infectious prion protein to temperature in a first elevated temperature range, followed by (b) cooling the infectious prion protein to lower elevated temperature in a second elevated temperature range, and (c) exposing the infectious prion protein to a proteolytic enzyme effective at such lower elevated temperature to degrade the infectious prion protein to a benign degradation product.

A still further aspect of the invention relates to a method of at least partially degrading infectious prion protein in tissue containing or contaminated with same, by steps including heating the tissue and simultaneously exposing same to a thermal stable proteolytic enzyme, at sufficient temperature and for sufficient time to at least partially degrade the infectious prion protein.

In another particular aspect, the invention relates to a method of processing an animal meat product or by-product to clear BSE-mediating infectious prion protein therefrom, the method comprising treating the animal meat product or by-product with a protease under sufficient temperature and for sufficient time to destroy the BSE-mediating infectious prion protein therein.

The invention relates in a still further aspect to a method of processing an animal meat product or by-product, including treating the animal meat product or by-product with a protease that is effective for destruction of any infectious prion protein associated therewith. The infectious prion protein may for example be a prion protein that is infectious for a transmissible spongiform encephalopathy (TSE).

In one compositional aspect, the invention relates to a tissue composition comprising (i) tissue containing or contaminated with an infectious prion protein and (ii) a proteolytic enzyme that is thermally stable in a temperature range of from about 35° C. to about 100° C.

Other aspects, features and embodiments of the invention will be more fully apparent from the ensuing disclosure and appended claims.

BRIEF DESCRIPTION OF THE DRAWING

FIG. 1 illustrates gel electrophoresis/Western blot results on SDS-PAGE gel, evidencing the efficacy of the method of the invention for destruction of infectious prion protein.

DETAILED DESCRIPTION AND PREFERRED EMBODIMENTS OF THE INVENTION

Relative to the present invention and its features, aspects and embodiments as more fully described hereinafter, the disclosures of the technical literature cited in the Background of the Invention section hereof, as well as the following patents and technical literature articles, are hereby incorporated herein by reference in their respective entireties:

U.S. Pat. Nos.: 4,908,220; 4,959,311; 5,063,161; 5,171,682; 5,186,961; and 5,712,147;

Deslys, J. P., "Screening slaughtered cattle for BSE," Nature, Vol. 409, pp. 476–477, Jan. 25, 2001; and Cohen, F. E., "Protein Misfolding and Prion Diseases," J. Mol. Biol. (1999), Vol. 293, pp. 313–320.

The present invention is based on the use of proteolytic enzymes for degradation of infectious prion protein in tissue.

The efficacy of the process of the present invention for degradation of the infectious prion protein is wholly unexpected since high temperature exposure (e.g., at 200° C.) of infectious prion proteins alone does not alter their pathogenic character; additionally, proteolytic enzymes such as proteinase K that fully digest non-infectious $PrP^{c}$ do not destroy the corresponding infectious isoform. It therefore is highly surprising that temperatures well below the incineration temperatures heretofore necessary for destruction of infectious $PrP^{Sc}$ can be employed for enzymatic treatment, to totally eliminate infectious $PrP^{Sc}$ from tissue containing or contaminated with same.

As used herein, the term elevated temperature means temperature of at least 35° C. The term proteolytic susceptibility means the ability of an infective prion protein to be enzymatically degraded to a non-infective product.

The treatment of tissue for reduction of infective prion protein associated therewith, can be carried out by various techniques as hereinafter described.

For example, the tissue (which may contain, be contaminated with, or be suspected to contain or be contaminated with, infectious prion protein) in one embodiment of the invention is heated to a sufficient temperature and for sufficient time to enhance the proteolytic susceptibility of infective prion protein that may be present, in conjunction with exposure of the tissue to a proteolytic enzyme that is effective to at least partially destroy any infective prion protein that is present.

Such treatment can be carried out in a two-step sequence, including an initial step of heating the tissue to a first higher elevated temperature and then exposing the heated tissue to the enzymatic agent at a second lower elevated temperature, for proteolytic degradation of the infectious prion protein.

In such two-step process, the tissue can be thermally treated, e.g., cooked, at first higher elevated temperature, and then cooled to second lower elevated temperature, e.g., by radiative heat loss from the tissue, convective cooling of the tissue, or in other appropriate manner, so that the tissue is at a suitable temperature when it is inoculated with or otherwise exposed to the proteolytic enzyme in the second enzymatic treatment step.

In the second step of such two-step process, the tissue is exposed to a proteolytic enzyme that is effective to at least partially destroy the infective protein prion associated with the tissue.

The method can therefore be carried out in various embodiments in which proteolytic susceptibility of infective prion protein in the tissue is enhanced by heating of the tissue to an elevated temperature for subsequent proteolytic enzyme treatment. The elevated temperature in the heating step may be any suitable temperature, e.g., at least 35° C., at least 40° C., at least 60° C., at least 75° C., and/or no more than 150° C. (or other lower temperature, as desired), with one illustrative specific temperature range being from about 100° C. to about 150° C., and more preferably from about 125° C. to about 140° C.

Alternatively, the prion protein destruction treatment of the invention may be carried out in a single-step procedure, in instances where the proteolytic enzyme is stable and effective (to remove the infectious prion protein) at the corresponding temperature used in the treatment process, so that no initial heating step is required.

In the single step method, the tissue and the proteolytic enzyme are heated to a suitable elevated temperature for the enzymatic degradation of the infectious prion protein to occur.

For example, the method of at least partially degrading infectious prion protein in tissue containing or contaminated with same, can be carried out by heating the tissue and simultaneously exposing same to a thermal stable proteolytic enzyme, at sufficient temperature and for sufficient time to at least partially degrade the infectious prion protein.

Regardless of the specific sequence of method steps employed in the practice of the invention, the tissue is exposed to a proteolytic enzyme (in the second step of the two-step method, or in the enzymatic degradation step of the single-step method) that is effective to at least partially destroy the infective protein prion in such tissue.

The enzymatic degradation step can be carried out at any suitable temperature in the practice of the invention, e.g., at a temperature above about 35° C., above about 40° C., or above about 50° C., depending on the nature of the proteolytic enzyme employed.

By way of illustrative examples, the enzymatic degradation step can be conducted at a temperature in a range of from about 35° C. to about 100° C., from about 40° C. to about 100° C., from about 50° C. to about 100° C., from about 40° C. to about 75° C., or from about 50° C. to about 60° C., depending on the proteolytic stability and enzymatic activity of the specific proteolytic enzyme that is employed.

In the enzymatic degradation step, the proteolytic enzyme at least partially, and preferably completely, destroys the infective protein prion that is in or otherwise associated with the tissue.

Temperature in the enzymatic treatment may be widely varied in the broad practice of the invention, depending on the thermostable character of the protease that is used to degrade the infectious prion protein.

It will be recognized that any of a wide variety of proteases may be employed in the practice of the invention, and that the choice of specific proteolytic enzyme will affect the choice of temperature that is used to carry out the proteolytic degradation, as well as the choice of any elevated temperature treatment of the tissue before its exposure to the proteolytic enzyme.

Specific temperature treatment conditions for the enzymatic treatment, as well as the temperature conditions necessary or desirable for any elevated temperature initial treatment step(s) that precede such enzymatic treatment, can be readily empirically determined without undue experimentation, within the skill of the art.

In the method of the invention, the tissue being treated may be of any suitable type, including mammalian as well as non-mammalian animal tissues, and even plant tissues that actually or potentially contain infectious prion proteins. Mammalian tissues can include human as well as non-human mammalian tissues.

In a specific aspect, the tissues treatable in the method of the invention include, without limitation, bovine tissue, ovine tissue, simian tissue, and human tissue, and include various tissue types, e.g., brain, pituitary, intestine, lung, heart, kidney, and/or spleen tissue. In one aspect, the method of the invention is employed to treat nervous system tissue, which may be central nervous system tissue and/or peripheral nervous system tissue.

Proteolytic enzymes usefully employed in the practice of the invention include enzymes that are enzymatically active and effective at the conditions of their use. For elevated temperature enzymatic treatment, the proteolytic enzyme is suitably thermostable at the conditions of use.

In this respect, proteolytic enzymes of widely varying thermostable character are known. For example, various proteolytic enzymes employed in specific embodiments of the invention may be thermostable up to 35° C., 40° C., 50° C., 60° C. or even 100° C.

The proteolytic enzyme may be of any suitable type, and may comprise a single enzymatic species, or alternatively a mixture of enzymes. The enzymes may be usefully employed in a free (unbound) form, or alternatively may be immobilized on a substrate for purposes of the tissue treatment step.

Illustrative proteolytic enzymes in the broad practice of the present invention include, without limitation, keratinase enzymes, proteinase K, trypsins, chymotrypsins, pepsins, chymosins, cathepsins, subtilisins, elastases, collagenases, endopeptidases, peptidases, oligopeptidease, thermolysins, bacillolysin, mycilysins, carboxypeptidases, leucyl aminopeptidases, aminopeptidases, and extremthermophilic proteases.

Preferred enzyme species include keratinase enzymes. A particularly preferred keratinase comprises *Bacillus licheniformis* PWD-1 keratinase. Proteolytic enzyme species useful in the practice of the invention include active fragments of proteolytic enzymes, e.g., an active fragment of a keratinase enzyme, such as the *Bacillus licheniformis* PWD-1 keratinase.

The method of enzymatically removing infectious prion proteins from tissue, in accordance with the present invention, can further include the step(s) of testing the tissue to verify destruction of infective prion protein therein, after proteolytic enzymatic treatment has been concluded.

The enzymatic treatment method of the invention can be carried out in any suitable manner, with any appropriate sequence of processing steps.

For example, in one embodiment, the tissue to be treated for removal of infectious prion proteins is subjected to initial non-enzymatic thermal treatment as necessary or desired, followed by enzymatic treatment for destruction of infective or contaminative prion protein, followed by testing of the tissue, and further thermal/enzymatic treatment (e.g., in an alternating and repetitive cycle of non-enzymatic thermal treatment, and enzymatic elevated temperature treatment), as required, if the post-treatment testing shows incomplete removal of the infectious prion protein from the tissue.

In another embodiment, infectious prion protein is at least partially degraded in tissue containing or contaminated with same, by steps including heating the tissue and simultaneously exposing same to a thermal stable proteolytic enzyme, at sufficient temperature and for sufficient time to at least partially degrade the infectious prion protein. The treated tissue then may be subjected to testing to characterize the removal of the infectious prion protein.

The testing of the tissue for infectious prion protein may be carried out in any suitable manner and with any suitable testing technique or methodology, e.g., by subjecting the tissue to a Western blot test, sandwich immunoassay test, ELISA test, fluoroimmunoassay test, capillary immunoelectrophoresis test, plasminogen binding test, or other suitable test that is efficacious for determining the presence or absence of infectious prion protein in the tissue being treated.

Further, the method of the invention may include an initial determination of the presence of infectious prion protein in the tissue being treated, before any thermal/enzymatic treatment, so that treatment is only applied to tissue that is established by such determination as containing infectious prion protein.

Alternatively, the thermal/enzymatic treatment may be administered to tissue that may potentially contain or be contaminated with, but is not definitively ascertained beforehand to verify the presence of, infective prion protein, followed by testing of the treatment product for determination of the presence or absence of any infectious prion protein therein.

The method of the invention is efficaciously applied to destroy infectious prion proteins in meat and meat by-products that are susceptible to containing or being contaminated with infectious prion proteins mediating TSEs such as BSE.

As such, the method of the invention provides a reliable approach to the treatment of bovine and other animal products and by-products that then can be further processed in food processing and/or rendering operations, rather than being incinerated to avoid transmission of BSE and other infectious prion protein diseases.

The invention thus contemplates in one embodiment a method of processing animal products and by-products, in which the prion protein is initially non-enzymatically thermally treated, e.g., by heating to a temperature that is below the pyrolytic destruction temperature (>>200° C.) of the infectious prion protein (at which incineration is generally conducted), followed by enzymatic degradation of the infectious prion protein.

In a specific illustrative embodiment of the invention, infective prion protein is removed from bovine tissue containing same, by cooking the bovine tissue at temperature in a range of from about 100° C. to about 150° C., e.g., for a time of from about 5 minutes to about 5 hours, followed by exposing the bovine tissue to a proteolytic enzyme at temperature in a range of from about 35° C. to about 100° C. at which the proteolytic enzyme is thermally stable and proteolytically effective to destroy the infective prion protein in the bovine tissue.

The cooking treatment can be carried out in a suitable chamber or vessel in which elevated temperature conditions are appropriately maintained, optionally with control of pressure to provide a desired atmospheric, sub-atmospheric, or superatmospheric pressure in the cooking operation.

After cooking, the bovine tissue is subjected to proteolytic enzymatic treatment with *Bacillus licheniformis* PWD-1 keratinase to destroy all infectious prion protein therein. Following the thermal/enzymatic treatment, the tissue may be processed in any suitable manner.

For example, such bovine tissue, e.g., after testing or assay verification of the complete destruction of infectious prion protein, can be processed to yield an animal feed ingredient (e.g., meat bone meal) or feed supplement.

In one particularly preferred process embodiment, the cooking step is carried out in a first elevated temperature range of from about 125° C. to about 150° C., and enzymatic treatment of the bovine tissue thereafter is carried out using *Bacillus licheniformis* PWD-1 keratinase, in a second elevated temperature range of from about 40° C. to about 60° C.

The method of the present invention enables the utilization of rendered bovine meat by-products that would otherwise (in suspicion or verification of the presence of infectious prion proteins), require incineration and disposal.

The inventive method thereby achieves a substantial advance in the art, permitting nutritional use of material that would otherwise, in the absence of treatment, constitute a biological hazard. The inventive method concurrently avoids the costs and infrastructure requirements for incineration and disposal of infected or contaminated animal tissue.

The invention embodies a simple methodology for removing infectious prion protein, e.g., BSE-mediating prion protein, from tissue, by exposing the tissue to a proteolytic enzyme that is thermally stable, at sufficient temperature and for sufficient time to at least partially clear the infectious prion protein from the tissue.

The method of the invention is broadly applicable to the destruction of prion protein that is infectious for transmissible spongiform encephalopathy (TSE) and/or for other prion protein-mediated diseases, including, without limitation, bovine spongiform encephalopathy (BSE) and sheep scrapie.

The method of the invention has applicability to processing animal meat for human food and processing of animal by-product for animal feed or an animal feed ingredient.

The present invention in one compositional aspect comprehends a tissue composition including (i) tissue, e.g., bovine tissue, containing an infectious prion protein, such as prion protein mediating BSE, and (ii) a proteolytic enzyme, e.g., *Bacillus licheniformis* PWD-1 keratinase, that is thermally stable in the temperature range employed for enzymatic treatment, e.g., from about 40° C. to about 60° C.

Such tissue composition may be at elevated temperature. The composition is enzymatically reactive at suitable elevated temperature to produce a product composition including the proteolytic enzyme and the treated tissue free of infectious prion protein.

While the invention has been illustratively described hereinabove primarily in application to the treatment of infected or contaminated animal tissue in a harvested state, such as rendered animal parts for the subsequent production of animal feed ingredients, the invention also comprehends the application of proteolytic enzymes for in vivo treatment of prionic diseases.

In one such embodiment, a therapeutic composition is provided for in vivo prionic disease treatment, including as an active ingredient a proteolytic enzyme that is combatingly effective against the prionic disease.

Another embodiment includes a therapeutic composition containing a keratinase in combination with a non-infectious prion protein (e.g., $PrP^c$, or a $PrP^{Sc}$ that has been modified to render same non-infectious, or a non-infectious fragment of $PrP^{Sc}$) serving as a molecular recognition protein for the infectious prion protein in vivo.

Still other therapeutic compositions are contemplated that include a keratinase or other proteolytic enzyme in vectorized constructs or combinations.

Another illustrative therapeutic composition includes a pyrogenic agent, such as a non-toxic modified endotoxin analog, in combination with a proteolytic enzyme that is combatingly effective against the prionic disease upon induction of pyrogenesis in vivo.

The invention also comprehends in vivo therapeutic compositions, comprising a polynucleotide sequence including a first region coding for the production of the proteolytic enzyme or active fragment thereof, and a second region coding for a pyrogenic peptide, as part of a recombinant polynucleotide expression vector. Following transfection, the in vivo expression of the thermotolerant proteolytic enzyme or active fragment thereof, and the pyrogenic peptide, effect infectious prion protein-combating action.

As a still further example, the therapeutic composition may in application to transmissible spongiform encephalopathy be formulated with a blood-brain barrier traversing agent, such as an amphiphilic drug-oligomer conjugate capable of traversing the blood-brain barrier. Such composition can comprise the therapeutic compound, e.g., keratinase or other proteolytic enzyme, or an active fragment thereof, conjugated to an oligomer, wherein the oligomer comprises a lipophilic moiety coupled to a hydrophilic moiety. Oligomers useful for formulating such therapeutic compositions are more fully described in International Publication WO 00/09073 published Feb. 24, 2000.

The features and advantages of the invention are more fully shown with reference to the following illustrative example.

EXAMPLE

A feather-degrading bacterium, *Bacillus licheniformis* strain PWD-1, isolated from a thermophilic anaerobic digester for poultry waste (see C. M. Williams and J. C. H. Shih, *J. Appl. Bacteriol.* 67, 25 (1989); J. C. H. Shih, *Poultry Sci.* 72, 1617 (1993)) was the source of the keratinase enzyme (see X. Lin, C. G. Lee, E. S. Casale, and J. C. H. Shih, *Appl. Environ. Microbiol.* 58, 3271 (1992)) employed in this example.

The gene encoding this keratinase enzyme (see X. Lin, D. W. Kelemen, E. S. Miller and J. C. H. Shih, *Appl. Env. Microbiol.* 61, 1469 (1995)) has been isolated and sequenced, and scale-up fermentation production of this enzyme has also been accomplished (see J. J. Wang and J. C. H. Shih, J. Ind. *Microb. Biotech.* 22, 608 (1999)). This enzyme is a serine protease.

Crude and purified preparations of this keratinase were produced as previously described (see X. Lin, C. G. Lee, E. S. Casale, and J. C. H. Shih, *Appl. Environ. Microbiol.* 58, 3271 (1992) and J. J. Wang and J. C. H. Shih, *J. Ind. Microb. Biotech.* 22, 608 (1999)) and obtained from the Fermentation Facility at North Carolina State University, Raleigh, N.C. (NCSU). The test for the effect of keratinase on PrP was carried out at Institute of Animal Science and Health at Lelystad (ID-Lelystad), The Netherlands.

Purified keratinase was compared with other proteases, including elastase, collagenase, proteinase K and trypsin (all from Sigma chemical Co.) in reacting with various kinds of substrates. Hydrolysis of keratin, elastin and collagen were measured by ninhydrin color reaction ($A_{450}$) of increased free amino groups (see X. Lin, C. G. Lee, E. S. Casale, and J. C. H. Shih, *Appl. Environ. Microbiol.* 58, 3271 (1992)). Free leucine was used as the standard to calculate the equivalent free amino groups. Casein hydrolysis was measured by the increased $A_{280}$ in the supernatant (see Price and Johnson, 1989). The results are presented in Table 1 below. For each given substrate, relative activities of all proteases were determined. Cumulative relative activity (CRA) demonstrated that the keratinase has a wide range of substrates and possesses high activity.

TABLE 1

Relative specific activities of proteases against different substrates[a]

| Substrate | Keratinase | Elastase | Collagenase | Proteinase K | Trypsin |
|---|---|---|---|---|---|
| Keratin[b] | 1.00 | 0.29 | 0.00 | 0.36 | 0.09 |
| Elastin[b] | 2.52 | 1.00 | 0.43 | 0.57 | 0.61 |
| Collagen[b] | 2.58 | 1.15 | 1.00 | 0.70 | 0.38 |
| Caseine[c] | 1.28 | 0.80 | 0.02 | 1.00 | 0.40 |
| CRA[d] | 7.38 | 3.24 | 1.45 | 2.63 | 1.48 |

[a]All enzyme activities were measured at their individual optimum conditions and compared.
[b]Proteolysis measured by ninhydrin reaction (Lin et al., 1992).
[c]Proteolysis measured by increased soluble $A_{280}$ (Price and Johnson, 1989).
[d]Cumulative Relative Activity.

The test of the effect of keratinase on pathogenic PrP was carried out in an Isolation Facility in the Laboratory of Molecular Recognition, ID-Lelystad. The European Union-validated procedure of Prionics Check (Prionics AG, Zurich) was used to detect pathogenic PrP. The Prionics Check procedure is based on the Western blot technique and employs 6H4 monoclonal antibody to visualize the specific form of PrP (Prionics AG, Test for the Detection of BSE-prions in Cattle, Practical Product Information, Zurich (2000)).

In order to mimic a meat bone meal process, modifications were made from the original procedure. First, proteinase K in the standard procedure was replaced by keratinase. A crude preparation of keratinase was used. Second, the effect of a pre-cooking of the BSE tissue was tested. The homogenized tissue was cooked at 115° C. for 40 minutes with a Vulcain pressure-cooker. Third, an anti-oxidant, sodium sulfite ($Na_2SO_3$), also was tested. The rest of the procedure was the same as described in the manufacturer's Practical Product Information (Prionics AG, Test for the Detection of BSE-prions in Cattle, Practical Product Information, Zurich (2000)).

The following protocol was employed. One g of BSE-positive brain tissue was mixed and homogenized with 9 ml of Prionics buffer. Half of the aliquot, 5 ml, was added with $Na_2SO_3$ to give a final concentration 0.1% and the other half, without $Na_2SO_3$. The aliquots were distributed 4×2.0 ml into autoclavable Falcon tubes. An additional 1.0 ml was for used for positive control, treated by the standard Prionics procedure, and another 1.0 ml, for no keratinase control. Two tubes, with and without $Na_2SO_3$, were pressure-cooked for 40 min and the other 2 tubes were not cooked. In the wells of the PCR plate, the samples, 150 µl each, were treated by keratinase (150 µg, 1,000 EU/mg) at 50° C. for 0-time or 4 hrs. Keratinase was pre-dissolved in phosphate buffer, 0.05 M, pH 7.5. The reaction was stopped by the addition of Prionics Pefabloc, an inhibitor of serine protease. At the end of enzymatic incubation, 10 µl of each sample mixture was loaded onto SDS-PAGE gel, and the Prionics procedure of electrophoresis, Western blot, and immuno-chemiluminescence detection was followed.

The results of this experiment are shown in FIG. 1 (effect of keratinase degradation on BSE-prion protein), wherein Lanes 1–17 are as follows:
Lane 1: buffer alone.
Lane 2: BSE-brain tissue as tested.
Lane 3: Pre-cooked with $Na_2SO_3$, keratinase stopped at 0-time.
Lane 4: Same as Lane 3, except keratinase digestion for 4 hr.
Lane 5: Pre-cooked without $Na_2SO_3$, keratinase stopped at 0-time.
Lane 6: Same as Lane 5, keratinase digestion for 4 hr.
Lane 7: Without pre-cooking, with $Na_2SO_3$, keratinase 0-time.
Lane 8: Same as Lane 7, except keratinase digestion 4 hr.
Lane 9: Without pre-cooking, without $Na_2SO_3$, keratinase 0-time.
Lane 10: Same as Lane 9, except keratinase digestion 4 hr.
Lane 11: Without pre-cooking, with $Na_2SO_3$, no keratinase.
Lane 12: Same as Lane 11, except incubation 4 hr (Note: keratinase was accidentally added).
Lane 13: Purified scrapie PrP with $Na_2SO_3$, keratinase stopped at 0-time.
Lane 14: Same as Lane 13, except keratinase digestion 4 hr.
Lane 15: Purified scrapie PrP with $Na_2SO_3$, without keratinase.
Lane 16: Same as Lane 15, except incubation 4 hr.
Lane 17: PrP standard.

As shown in FIG. 1, the digestive effect of keratinase on infectious PrP is evident, particularly when the samples were precooked at 115° C. for 40 min (Lanes 3–6). Without precooking (Lanes 7–10), the keratinase was less effective, but keratinase still degraded more than half of the infectious PrP positive material. On purified sheep scrapie PrP, keratinase was found to be active as well (Lanes 13–16). The presence of $Na_2SO_3$ did not appear to make much difference (Lanes 15–16) either alone or with keratinase. The Lane 12 sample was accidentally added with keratinase and therefore was positive.

These results demonstrate the versatility of the keratinase in degrading all types of proteins tested. In the test of the efficacy of the keratinase on BSE PrP, the results were positive, especially when the BSE brain tissue samples were pre-cooked. This is the first experiment to demonstrate that pathogenic PrP is degradable by an enzyme.

Pressure cooking at temperatures on the order of 125° C. is a routine step in processing animal by-products into meat bone meal. Post-cooking treatment with keratinase in accordance with the invention, for destruction of infectious PrP, provides an effective method to control the spread of BSE. The keratinase-treated meat bone meal is readily tested to verify the absence of PrP, so that the meat bone meal can be recycled for feed use.

The method of the invention thus provides a simple and useful enzymatic treatment for animal product and by-product processing.

While the invention has been described herein with reference to various illustrative features, aspects, and embodiments, it will be appreciated that the utility of the invention is not thus limited, but rather extends to and encompasses other variations, modifications and other embodiments, as will readily suggest themselves to those of ordinary skill in the art.

Accordingly, the invention is to be broadly interpreted and construed as including such other variations, modifications and other embodiments, within the spririt and scope of the invention as hereinafter claimed.

What is claimed is:

1. A method of treatment of tissue for destruction of infective prion protein therein, the method comprising the steps of:
   (a) providing said tissue in a form in which said infective prion is accessible for enzymatic exposure;
   (b) heating the tissue to a temperature in a range of about 35–150° C. for a sufficient period of time to enhance proteolytic susceptibility of said infective prion protein therein;
   (c) exposing the heated tissue to *Bacillus licheniformis* PWD-1 keratinase at a temperature in a range of about 35–100° C. for a sufficient period of time; and
   (d) verifying destruction of infective prion protein in the tissue.

2. A method of treatment of tissue for destruction of infective prion protein therein, the method comprising the steps of:
   (a) providing said tissue in a form in which said infective prion is accessible for enzymatic exposure;
   (b) exposing the tissue to Bacillus licheniformis PWD-1 keratinase at a temperature in a range of about 35–100° C. for a sufficient period of time to degrade the prion protein; and
   (d) verifying destruction of infective prion protein in the tissue.

3. A method of treatment of tissue for reduction of infective prion protein therein, the method comprising the steps of:
   (a) providing said tissue in a form in which said infective prion protein is accessible for enzymatic exposure;
   (b) heating the tissue to a temperature in a range of from about 100° C. to about 150° C. and for sufficient time to enhance the proteolytic susceptibility of said infective prion protein therein; and
   (c) exposing the heated tissue to a proteolytic enzyme that is effective for at least partial reduction of the infective prion protein in such tissue.

4. A method of treatment of tissue for reduction of infective prion protein therein, the method comprising the steps of:
   (a) providing said tissue in a form in which said infective prion protein is accessible for enzymatic exposure;
   (b) heating the tissue to a temperature in a range of from about 125° C. to about 140° C. and for sufficient time to enhance the proteolytic susceptibility of said infective prion protein therein; and
   (c) exposing the heated tissue to a proteolytic enzyme that is effective for at least partial reduction of the infective prion protein in such tissue.

5. A method of reducing infective prion protein in bovine tissue containing or contaminated with same, the method including (a) providing said animal tissue in a form in which said infectious prion protein therein is accessible for enzymatic exposure, (b) cooking the bovine tissue at a temperature in a range of from about 100° C. to about 150° C., followed by (c) exposing the bovine tissue to a proteolytic enzyme at a temperature in a range of from about 35° C. to about 100° C. at which the proteolytic enzyme is thermally stable and proteolytically effective to destroy the infective prion protein associated with the bovine tissue, wherein said proteolytic enzyme is selected from the group consisting of keratinase and subtilisins.

6. The method of claim 5, wherein said cooking is conducted for a time of from about 5 minutes to about 5 hours.

7. The method of claim 5, wherein the proteolytic enzyme comprises *Bacillus licheniformis* PWD-1 keratinase.

8. A method of degrading an infectious prion protein contained in an animal tissue, comprising (a) homogenizing said animal tissue containing said infectious prion protein, (b) heating the animal tissue containing the infectious prion protein to a first temperature in a first elevated temperature range of from about 125° C. to about 150° C., followed by (c) cooling the animal tissue containing the infectious prion protein to a second temperature that is lower than the first temperature and is in a second elevated temperature range of from about 35° C. to about 60° C., and (d) exposing the animal tissue containing the infectious prion protein to a proteolytic enzyme effective at such second, lower temperature to degrade the infectious prion protein, wherein the proteolytic enzyme is selected from the group consisting of keratinase and subtilisins.

9. A method of destroying infectious prion protein in tissue containing or contaminated with same, wherein said tissue comprises bovine or ovine tissue, said method comprising homogenizing said tissue, cooking said tissue at a temperature in a range of from about 100° C. to about 150° C. and for a time in a range of from about 5 minutes to about 5 hours, followed by contacting said tissue with *Bacillus licheniformis* PWD-1 keratinase at a temperature in a range of from about 35° C. to about 100° C. for sufficient time to destroy said infectious prion protein in said tissue.

* * * * *